United States Patent
Criscuolo et al.

(10) Patent No.: US 9,987,114 B2
(45) Date of Patent: Jun. 5, 2018

(54) COMBINATION THREE-DIMENSIONAL SURGICAL IMPLANT

(75) Inventors: Christopher J. Criscuolo, Branford, CT (US); Anthony Arena, Stratford, CT (US); Luis Restrepo, Fairfield, CT (US); Matthew D. Cohen, Berlin, CT (US); Joseph Hotter, Middletown, CT (US)

(73) Assignee: Covidien LP, Mansfield, MA (US)

(*) Notice: Subject to any disclaimer, the term of this patent is extended or adjusted under 35 U.S.C. 154(b) by 1225 days.

(21) Appl. No.: 13/636,903

(22) PCT Filed: Mar. 24, 2011

(86) PCT No.: PCT/US2011/029813
§ 371 (c)(1),
(2), (4) Date: Feb. 7, 2013

(87) PCT Pub. No.: WO2011/119845
PCT Pub. Date: Sep. 29, 2011

(65) Prior Publication Data
US 2013/0138124 A1    May 30, 2013

Related U.S. Application Data

(60) Provisional application No. 61/317,020, filed on Mar. 24, 2010.

(51) Int. Cl.
*A61B 17/08* (2006.01)
*A61F 2/00* (2006.01)

(52) U.S. Cl.
CPC .... *A61F 2/0063* (2013.01); *A61F 2002/0068* (2013.01); *A61F 2210/0004* (2013.01);
(Continued)

(58) Field of Classification Search
CPC ............ A61F 2/0063; A61F 2002/0068; A61F 2210/0004; A61F 2220/0083; A61F 2250/0031
See application file for complete search history.

(56) References Cited

U.S. PATENT DOCUMENTS 5,092,884 A     3/1992   Devereux et al.
5,254,133 A  *  10/1993  Seid .................. A61B 17/0057
                                                        128/899
(Continued)

FOREIGN PATENT DOCUMENTS

EP          614650 A2    9/1994
FR          2766698 A1   2/1999
(Continued)

OTHER PUBLICATIONS

European Search Report, Application No. 11760226 dated Aug. 3, 2015.
(Continued)

*Primary Examiner* — Gregory Anderson
*Assistant Examiner* — Sarah Simpson

(57) ABSTRACT

The present disclosure provides a compound three-dimensional surgical implant and methods of forming and using the same. The compound three-dimensional surgical implant includes a grip-type knit mesh defining pores and including a plurality of spiked naps extending from a surface the grip-type knit mesh, a prosthetic knit mesh defining principal cells and peripheral cells being layered on the grip-type knit mesh such that at least a portion of the spiked naps grip at least a portion of the cells of the prosthetic knit mesh. The grip-type knit mesh and the prosthetic knit mesh are folded together into a predetermined three-dimensional structure such that at least a portion of the spiked naps grip at least a
(Continued)

portion of the pores of the grip-type knit mesh to hold the three-dimensional structure of the surgical implant.

17 Claims, 4 Drawing Sheets

(52) U.S. Cl.
CPC .............. *A61F 2220/0083* (2013.01); *A61F 2250/0031* (2013.01); *A61F 2250/0067* (2013.01)

(56) References Cited

U.S. PATENT DOCUMENTS

| | | | |
|---|---|---|---|
| 5,258,000 A | 11/1993 | Gianturco | |
| 5,284,034 A | 2/1994 | Weis et al. | |
| 5,290,217 A | 3/1994 | Campos | |
| 5,326,355 A | 7/1994 | Landi | |
| 5,356,432 A * | 10/1994 | Rutkow | A61B 17/0057 600/37 |
| 5,368,602 A | 11/1994 | de la Torre | |
| 5,385,036 A | 1/1995 | Spillane et al. | |
| 5,397,331 A | 3/1995 | Himpens et al. | |
| 5,399,419 A | 3/1995 | Porter et al. | |
| 5,428,024 A | 6/1995 | Chu et al. | |
| 5,445,599 A | 8/1995 | Edenbaum | |
| 5,460,962 A | 10/1995 | Kemp | |
| 5,569,273 A | 10/1996 | Titone et al. | |
| 5,593,441 A | 1/1997 | Lichtenstein et al. | |
| 5,595,571 A | 1/1997 | Jaffe et al. | |
| 5,607,590 A | 3/1997 | Shimizu | |
| 5,616,689 A | 4/1997 | Shenoy et al. | |
| 5,619,869 A | 4/1997 | Tacy | |
| 5,676,967 A | 10/1997 | Williams et al. | |
| 5,686,090 A | 11/1997 | Schilder et al. | |
| 5,695,525 A | 12/1997 | Mulhauser et al. | |
| 5,711,960 A | 1/1998 | Shikinami | |
| 5,716,409 A | 2/1998 | Debbas | |
| 5,725,557 A | 3/1998 | Gatturna et al. | |
| 5,743,917 A | 4/1998 | Saxon | |
| 5,756,678 A | 5/1998 | Shenoy et al. | |
| 5,785,983 A | 7/1998 | Furlan et al. | |
| 5,919,232 A | 7/1999 | Chaffringeon et al. | |
| 5,931,165 A | 8/1999 | Reich et al. | |
| 6,004,333 A | 12/1999 | Sheffield et al. | |
| 6,042,534 A | 3/2000 | Gellman et al. | |
| 6,080,194 A | 6/2000 | Pachence et al. | |
| 6,090,116 A | 7/2000 | D'Aversa et al. | |
| 6,113,623 A | 9/2000 | Sgro | |
| 6,158,255 A | 12/2000 | Ternon | |
| 6,162,962 A | 12/2000 | Hinsch et al. | |
| 6,166,184 A | 12/2000 | Hendriks et al. | |
| 6,196,032 B1 | 3/2001 | Rock et al. | |
| 6,197,935 B1 | 3/2001 | Doillon et al. | |
| 6,210,439 B1 | 4/2001 | Firmin et al. | |
| 6,214,020 B1 | 4/2001 | Mulhauser et al. | |
| 6,258,124 B1 | 7/2001 | Darois et al. | |
| 6,267,772 B1 | 7/2001 | Mulhauser et al. | |
| 6,287,316 B1 | 9/2001 | Agarwal et al. | |
| 6,287,344 B1 | 9/2001 | Wampler et al. | |
| 6,319,264 B1 | 11/2001 | Tormala et al. | |
| 6,346,515 B1 | 2/2002 | Pitaru et al. | |
| 6,383,201 B1 | 5/2002 | Dong | |
| 6,408,656 B1 | 6/2002 | Ory et al. | |
| 6,497,950 B1 | 12/2002 | Haile et al. | |
| 6,638,284 B1 | 10/2003 | Rousseau et al. | |
| 6,652,595 B1 | 11/2003 | Nicolo | |
| 6,673,370 B2 | 1/2004 | Burke et al. | |
| 6,685,714 B2 | 2/2004 | Rousseau | |
| 6,736,823 B2 | 5/2004 | Darois et al. | |
| 6,736,854 B2 | 5/2004 | Vadurro et al. | |
| 6,737,371 B1 | 5/2004 | Planck et al. | |
| 6,758,068 B2 | 7/2004 | Shirasaki et al. | |
| 6,761,908 B1 | 7/2004 | Roreger | |
| 6,783,554 B2 | 8/2004 | Amara et al. | |
| 6,790,438 B1 | 9/2004 | Constancis et al. | |
| 6,837,078 B1 | 1/2005 | Rock et al. | |
| 6,966,918 B1 | 11/2005 | Schuldt-Hempe et al. | |
| 7,011,688 B2 | 3/2006 | Gryska et al. | |
| 7,011,851 B2 | 3/2006 | Burke et al. | |
| 7,021,086 B2 | 4/2006 | Ory et al. | |
| 7,022,358 B2 | 4/2006 | Eckmayer et al. | |
| 7,060,103 B2 | 6/2006 | Carr, Jr. et al. | |
| 7,076,974 B1 | 7/2006 | Chen | |
| 7,087,065 B2 | 8/2006 | Ulmsten et al. | |
| 7,156,804 B2 | 1/2007 | Nicolo | |
| 7,174,750 B2 | 2/2007 | Shirasaki et al. | |
| 7,181,933 B2 | 2/2007 | Callaway et al. | |
| 7,198,638 B2 | 4/2007 | Dong | |
| 7,213,421 B2 | 5/2007 | Shirasaki et al. | |
| 7,235,504 B2 | 6/2007 | Shirasaki et al. | |
| 7,404,819 B1 | 7/2008 | Darios et al. | |
| 7,549,303 B2 | 6/2009 | Callaway et al. | |
| 7,594,921 B2 | 9/2009 | Browning | |
| 7,604,816 B2 | 10/2009 | Hiltner et al. | |
| 7,614,258 B2 | 11/2009 | Cherok et al. | |
| 7,732,354 B2 | 6/2010 | Fricke et al. | |
| 7,754,258 B2 | 7/2010 | Morgan et al. | |
| 7,820,794 B2 | 10/2010 | Lin et al. | |
| 7,858,741 B2 | 12/2010 | Raines et al. | |
| 2002/0116070 A1 | 8/2002 | Amara et al. | |
| 2004/0054376 A1 * | 3/2004 | Ory | A61F 2/0063 606/151 |
| 2004/0221431 A1 | 11/2004 | Wittmann | |
| 2005/0222591 A1 | 10/2005 | Gingras et al. | |
| 2005/0244455 A1 | 11/2005 | Greenawalt | |
| 2007/0260179 A1 | 11/2007 | Sholev et al. | |
| 2009/0036997 A1 * | 2/2009 | Bayon | A61L 27/38 623/23.75 |
| 2011/0087271 A1 * | 4/2011 | Sargeant | A61B 17/0057 606/213 |
| 2011/0166494 A1 * | 7/2011 | Calvez | A61F 2/0063 604/8 |

FOREIGN PATENT DOCUMENTS

| | | |
|---|---|---|
| WO | 9310731 A1 | 6/1993 |
| WO | WO 2009/016519 A2 | 2/2009 |

OTHER PUBLICATIONS

International Search Report corresponding to International Application No. PCT/US2011/029813, completed on May 9, 2011 and dated Jun. 7, 2011; 2 pages.

* cited by examiner

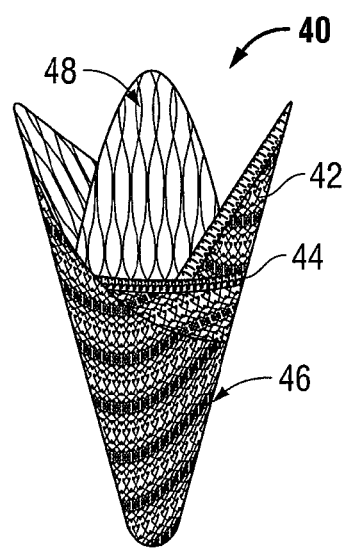
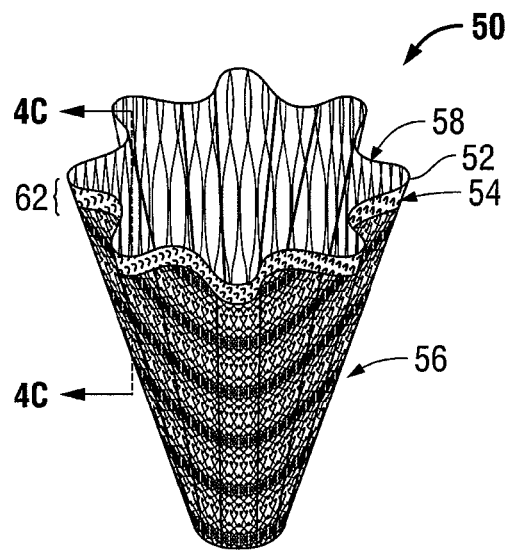
FIG. 4A    FIG. 4B
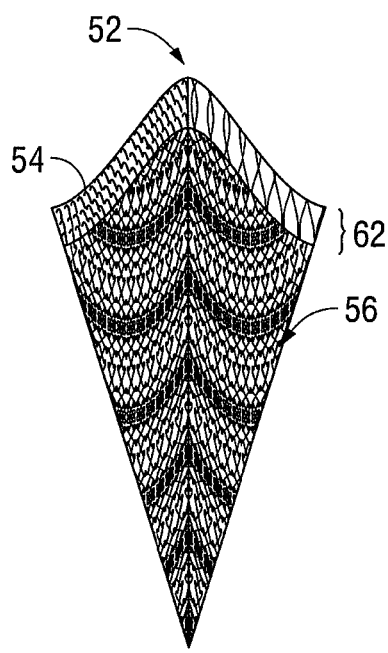
FIG. 4C

COMBINATION THREE-DIMENSIONAL SURGICAL IMPLANT

CROSS-REFERENCE TO RELATED APPLICATIONS

This application is a U.S. National Stage Application filed under 35 U.S.C. § 371(a) of International Application No. PCT/US2011/029813 filed Mar. 24, 2011, which claims the benefit of and priority to U.S. Provisional Patent Application Ser. No. 61/317,020 filed Mar. 24, 2010, the entire contents of which are incorporated by reference herein.

BACKGROUND

Technical Field

The present disclosure relates to implants or surgical meshes and, more particularly, to combination meshes that have a three-dimensional structure.

Description of the Related Art

Surgical meshes formed from degradable or non-degradable materials for use during both open and minimally invasive surgeries are known. These meshes are typically flat fibrous material that a surgeon places over a defect, such as a tear in tissue, as reinforcement. The surgeon then secures the mesh in place with a surgical fastener, such as a staple, clip, tack, suture or the like.

Meshes exhibiting structures other than a planar or flat structure are also known. These meshes form a plug to fill the defect. In some cases, these meshes are preformed from permanent rigid materials with pleats to create some form of flexibility. These permanent meshes can also require a separate flat mesh overlay to reinforce the defect.

Surgical meshes formed from non-degradable materials can be rigid. Rigid surgical meshes have benefits in hernia repair, for example, a rigid hernia mesh keeps the hernia sac retracted, is quicker and easier to use, and is inserted using an easily reproducible procedure. However, the non-degradable materials result in permanent foreign material inside a patient's body. The heavy non-degradable materials used to form rigid meshes also have small pore sizes, which can inhibit tissue in-growth.

Surgical meshes formed from degradable materials may produce a soft, pliant surgical mesh. The level of flexibility of a pliant mesh is controlled by the materials used to form the mesh and the weave or knitting of the mesh. For example, a large pore mesh formed from lightweight degradable materials has enhanced tissue in-growth and reduced inflammatory response following implantation; it also results in less scarring than a heavyweight, small pore mesh. A soft, pliant mesh will form to the abdominal wall of the patient's body and flex more naturally with the movement of the abdominal wall following implantation. Due to the more natural action of a flexible, pliant mesh the patient typically experiences less postoperative pain and improved comfort. However, meshes made solely from degradable material may not be suitable for long term hernia repair.

It would be advantageous to provide a surgical mesh formed of both non-degradable and degradable materials so as to produce a soft, pliant mesh providing improved comfort and less postoperative pain for the patient. It would also be advantageous to provide a surgical mesh that can be formed or reformed into a three-dimensional structure needed to fit the defect.

In particular, it would be advantageous to provide a surgical mesh that forms and maintains a three-dimensional structure during and following implantation, leaves little permanent foreign material inside a patient's body, and secures itself within the defect.

SUMMARY

The present disclosure provides a compound three-dimensional surgical implant, which includes a grip-type knit mesh defining pores and including a plurality of spiked naps extending from a surface the grip-type knit mesh and a prosthetic knit mesh defining principal cells and peripheral cells being layered on the grip-type knit mesh such that at least a portion of the spiked naps grip at least a portion of the cells of the prosthetic knit mesh. The grip-type knit mesh and the prosthetic knit mesh may be folded together into a predetermined three-dimensional structure such that at least a portion of the spiked naps grip at least a portion of the pores of the grip-type knit mesh to hold the three-dimensional structure of the surgical implant.

The present disclosure also provides a method of forming a compound three-dimensional surgical implant including: providing a grip-type knit mesh defining pores and including a plurality of spiked naps extending from a surface thereof; providing a prosthetic knit mesh defining principal cells and peripheral cells; placing the prosthetic knit mesh on the grip-type knit mesh such that at least a portion of the principal cells and/or peripheral cells and at least a portion of the spiked naps engage to fasten the prosthetic knit mesh to the grip-type knit mesh forming a compound surgical implant; fastening the compound surgical implant into a three-dimensional structure such that at least a portion of the pores of the grip-type mesh and at least a portion of the spiked naps of the grip-type mesh engage to fasten the compound surgical implant in the three-dimensional structure.

A method of hernia repair is also disclosed herein. The method includes: providing a compound surgical implant comprising pores and including a plurality of spiked naps extending from a surface thereof; forming the compound surgical implant into a compound three-dimensional structure such that at least a portion of the pores and at least a portion of the spiked naps engage to fasten the surgical implant into the compound three-dimensional structure; transferring said compound three-dimensional structure into a body cavity having a hernia; and placing the compound three-dimensional mesh in the hernia to repair the hernia.

Additionally, the disclosure provides a compound three-dimensional surgical implant. The implant includes a grip-type knit mesh defining pores and including a plurality of spiked naps extending from a surface thereof and a prosthetic knit mesh defining principal and/or peripheral cells located on the grip-type knit mesh whereby the spiked naps of the grip-type knit mesh grip the principal cells and/or peripheral cells of the prosthetic knit mesh forming a compound mesh and whereby the compound three-dimensional surgical implant is formed by folding the compound mesh into a predetermined three-dimensional structure such that at least a portion of the spiked naps grip at least a portion of the pores to hold the three-dimensional structure of the compound three-dimensional surgical implant.

BRIEF DESCRIPTION OF THE DRAWINGS

The foregoing objects and advantages of the disclosure will become more apparent from the reading of the following description in connection with the accompanying drawings, in which:

FIGS. 4A, 4B, and 4C are perspective views of the combination mesh following three-dimensional structure formation.

DETAILED DESCRIPTION

Figure 1:
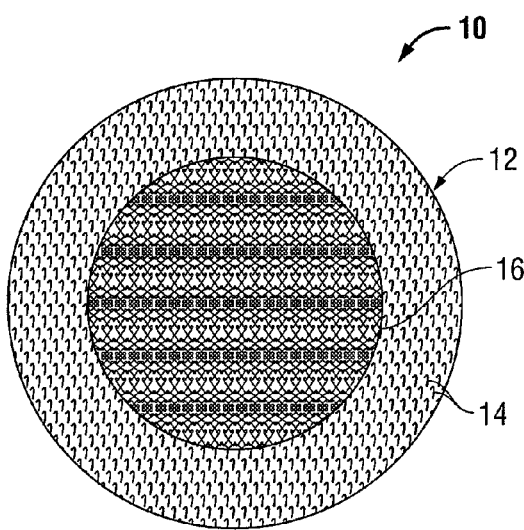
FIG. 1 is a is a top view of a combination mesh prior to forming a three-dimensional structure.

The present disclosure relates to a combination mesh folded into a three-dimensional configuration. The combination mesh includes at least a grip-type knit mesh and a smaller prosthetic knit mesh. Each component of the combination mesh may be formed from biodegradable materials, non-biodegradable materials, or a combination of these. A combination mesh formed from biodegradable and non-biodegradable materials produces a semi-absorbable mesh resulting in less implanted mass while still providing a strong rigid support to maintain the long term integrity of the repair. The thickness of the smaller prosthetic knit mesh on top of the grip-type knit mesh adds bulk to the combination mesh enhancing the stabilization of the three-dimensional structure and providing a bulking effect to more effectively retract the hernia sac and further safeguard against recurrence. The smaller prosthetic knit mesh also covers many of the spiked naps on the combination mesh allowing for ease of transport in situ and prevention of premature adherence to tissue. The grip-type portion exposed on the combination mesh allows for formation of a specific shape to fit the patient's defect and the three-dimensional structure may be maintained without the need for stitching, gluing or preforming the mesh to a specific structure.

The present disclosure relates to devices, systems, and methods for minimally invasive surgeries such as, endoscopic, laparoscopic, arthroscopic, endoluminal and/or transluminal placement of a surgical patch at a surgical site. As used herein the term "surgical mesh" is used to refer to any three-dimensional grip-type implant for use in surgical procedures, such as, for example, meshes that do not require suturing to the abdominal wall. Although described herein with reference to a hernia mesh, the method of the disclosure may be used in any surgical repair. As used herein the term "laparoscopic deployment device" is used to refer to a deployment device that may be used during minimally invasive surgeries described above. Although described herein with reference to a minimally invasive surgery, the surgical mesh may also be used in open surgery.

Materials

The fibers forming the combination mesh may be made from any fiber-forming biocompatible polymer. The biocompatible polymer may be synthetic or natural. The biocompatible polymer may be biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

Representative natural biodegradable polymers which may be used include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers which may be used include: cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic degradable polymers suitable for use include: polyhydroxy acids prepared from lactone monomers, such as glycolide, lactide, caprolactone, $\epsilon$-caprolactone, valerolactone, and $\delta$-valerolactone, as well as pluronics, carbonates (e.g., trimethylene carbonate, tetramethylene carbonate, and the like); dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-($\epsilon$-caprolactone-)); poly(glycolide-co-($\epsilon$-caprolactone)); polycarbonates; poly(pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof.

Some non-limiting examples of suitable non-bioabsorbable materials from which the fibers of the grip-type knit mesh and smaller prosthetic knit mesh may be made include: polyolefins, such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

Rapidly biodegradable polymers, such as poly(lactide-co-glycolide)s, polyanhydrides, and polyorthoesters, which have carboxylic groups exposed on the external surface as the smooth surface of the polymer erodes, may also be used. It should of course be understood that any combination of natural, synthetic, biodegradable, and non-biodegradable materials may be used to form the combination mesh.

In embodiments, the naps of the grip-type knit mesh are formed from polylactic acid (PLA) and the mesh is formed from a monofilament polyester of polyethylene terephthalate (PET). In embodiments, the smaller prosthetic mesh is formed from a polypropylene monofilament.

Bioactive Agents

The grip-type knit mesh and/or the prosthetic knit mesh may include a bioactive agent. The term "bioactive agent" as used herein, is used in its broadest sense and includes any substance or mixture of substances that have clinical use. Consequently, bioactive agents may or may not have pharmacological activity per se, e.g., a dye.

Alternatively, a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the implant in any suitable form of matter, e.g., films, powders, liquids, gels and the like.

The bioactive agent may be bound to the grip-type knit mesh and/or the smaller prosthetic knit mesh covalently, non-covalently, i.e., electrostatically, through a thiol-mediated or peptide-mediated bond, or using biotin-avidin chemistries and the like.

Examples of classes of bioactive agents, which may be utilized in accordance with the present disclosure include, for example, anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of bioactive agents may be used.

Anti-adhesive agents may be used to prevent adhesions from forming between the mesh and the surrounding tissues opposite the target tissue. In addition, anti-adhesive agents may be used to prevent adhesions from forming between the coated surgical implant and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which may be included as a bioactive agent include, for example: triclosan, also known as 2,4,4'-trichloro-2'-hydroxydiphenyl ether; chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin, tetracycline, aminoglycosides, such as tobramycin and gentamicin, rifampicin, bacitracin, neomycin; chloramphenicol; miconazole; quinolones such as oxolinic acid, norfloxacin, nalidixic acid, pefloxacin, enoxacin and ciprofloxacin; penicillins such as oxacillin and pipracil; nonoxynol 9; fusidic acid; cephalosporins; and combinations thereof. In addition, antimicrobial proteins and peptides such as bovine lactoferrin and lactoferricin B may be included as a bioactive agent.

Other bioactive agents which may be included are: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents which may be included in the grip-type knit mesh and/or the smaller prosthetic knit mesh include, for example, viruses and cells, including stem cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

Combination Mesh Structure

Formation of the combination mesh requires application of a prosthetic knit mesh in such a manner as to cover a portion of the spiked naps of a grip-type knit mesh. For example, the prosthetic mesh may cover ¼, ½, or ¾ of the grip-type knit mesh. The spiked naps of the grip-type knit mesh grip the cells of the prosthetic mesh to attach thereto.

After application of the prosthetic mesh, the amount of spiked naps remaining exposed should be sufficient to secure the combination mesh in a three-dimensional structure.

Referring now in specific detail to the drawings, in which like numbers identify similar or identical elements, FIG. 1 is an illustration of a combination mesh prior to forming a three-dimensional structure. The combination mesh 10 includes grip-type knit mesh 12, which has spiked naps 14.

The grip-type knit mesh also includes a porous side (not shown). Atop the grip-type knit mesh 12 is the prosthetic knit mesh 16. The spiked naps 14, grip into the open cell structure of the prosthetic knit mesh 16. Although the prosthetic knit mesh 16 is shown as covering a large portion of the grip-type knit mesh 12, the prosthetic knit mesh 16 may cover less or more of the grip-type knit mesh 12, as necessary to meet a patient's needs.

Grip-Type Knit Mesh Structure

The grip-type knit mesh may be knit from a monofilament sheet forming, on at least a portion of at least one face of the knit, spiked naps which protrude with respect to the sheet. In embodiments, the naps each have a substantially rectilinear body and, at the free end of this body, a head of greater width than that of the body.

This knit can be formed using a thermofusible monofilament to form a monofilament sheet, forming outer loop-shaped meshes in the sheet, and then partially fusing the monofilament.

The length of the spiked naps is defined so as to penetrate and fasten to a porous textile structure in a limited manner. In embodiments, the spiked naps fasten into the cells of the prosthetic knit mesh and the porous portion of the grip-type knit mesh, at different locations.

In embodiments, the monofilament forming the spiked naps can have a diameter from about 0.05 mm to about 0.15 mm, in embodiments a diameter of over 0.10 mm. Each spiked nap can have a length of from about 1 mm to about 2 mm, in embodiments a length of about 1.5 mm. The density of the spiked naps can be from about 50 to about 90 naps per square centimeter, in embodiments from about 65 to about 75 naps per square centimeter. Suitable grip-type knit meshes and methods for making them are disclosed in U.S. Pat. No. 7,331,199, the disclosure of which is incorporated by reference herein in its entirety.

The textile structure of the knit may include two faces, one with the spiked naps, and one with open pores, which for example may have a diameter of from about 1 mm and about 3 mm. For example, this structure can include several sheets of interlaced yarns, which together form a layered structure. When interlaced yarns are used, the layered structure may be composed, for example, of three sheets: an intermediate sheet of yarn distributed to form a zigzag openwork pattern between the columns of meshes; a front sheet of yarn distributed to form a chain stitch; and a rear sheet of monofilament placed in partial weft under the chain stitch and "thrown onto" the needle not forming a chain stitch, this sheet may include the spiked naps.

When a grip-type knit is applied, with spiked naps to the front, onto a surface of a porous prosthetic knit, the spiked naps engage into the mesh and between the multifilament yarns of the prosthetic knit and fasten the grip-type knit onto the prosthetic knit. This fastening, effective even in a liquid environment, is sufficient to secure the mesh in the desired three-dimensional structure and to offer mechanical resistance to tangential stresses, while at the same time permitting unfastening of the grip-type knit in order to adjust its position in relation to the element lying underneath, if desired.

In embodiments, the prosthetic knit portion of the mesh may include size markings. The size markings may indicate the location at which the grip-type knit may be secured to the prosthetic knit or to itself during manipulation into a three-dimensional configuration in order to obtain three-dimensional structures of various sizes. The markings may be any type of marking as is known in the art. For example, a dye or colorant may be placed (e.g., printed) at specific locations on the prosthetic knit. As another example, a colored yarn may be woven into specific locations of the prosthetic knit, grip-type knit or both. Those skilled in the art will readily envision other ways of applying suitable markings to the present meshes.

Figure 2A:
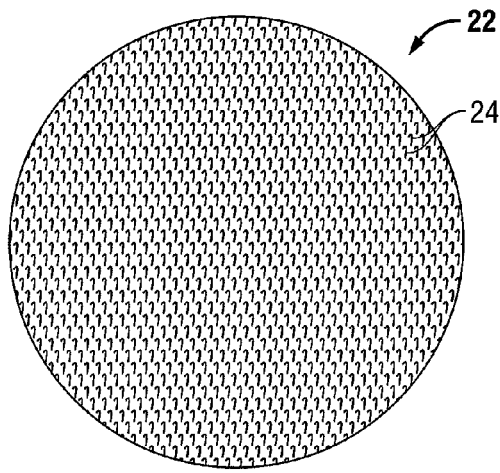
FIGS. 2A and 2B are top views of the grip-type knit mesh and the smaller prosthetic knit mesh prior to forming the combination mesh.

An illustration of a grip-type knit mesh prior to forming a three-dimensional structure is shown in FIG. 2A. The grip-type knit mesh 22 includes spiked naps 24. Although the spiked naps 24 are depicted as covering the entire grip-type knit mesh 22, the spiked naps 24 may cover less of the mesh.

The grip-type knit mesh 22 also includes a porous side (not shown). The spiked naps 24 grip into the open cell structure of the prosthetic knit during formation of the combination mesh. The spiked naps 24 also grip the porous side (not shown) of the grip-type knit mesh 22 during formation into a three-dimensional structure. It is also envisioned that the spiked naps 24 can cover a portion of each side of a mesh.

Prosthetic Knit Mesh Structure

The prosthetic knit mesh may include a biocompatible monofilament knit in an open-mesh unblocked weave having front and back walls of fabric. In embodiments, the monofilament has a diameter of between about 0.12 mm to about 0.18 mm, in embodiments about 0.15 mm. In embodiments, the monofilament has a diameter of between about 0.07 mm to about 0.14 mm, in embodiments about 0.08 mm to about 0.10 mm.

The knit of the prosthetic knit mesh can result in a mesh with substantially polygonal cells. The principal larger polygonal cells are surrounded by smaller peripheral cells. In embodiments, each of the principal cells has a diameter of from about 1 mm to about 2 mm, in embodiments between about 1.5 mm to about 1.9 mm. In embodiments, the peripheral cells have a diameter of between about 0.4 mm to about 0.8 mm, in embodiments between about 0.6 mm to about 0.7 mm. The smaller peripheral cells allow the spiked-naps of the grip-type mesh to grip the prosthetic knit mesh. The larger, principal cells allow for tissue ingrowth in situ.

Suitable prosthetic knit meshes are described in U.S. Pat. No. 6,408,656 and U.S. patent application Ser. No. 10/488,203 the disclosure of each of which is incorporated by reference herein in its entirety.

Figure 2B:
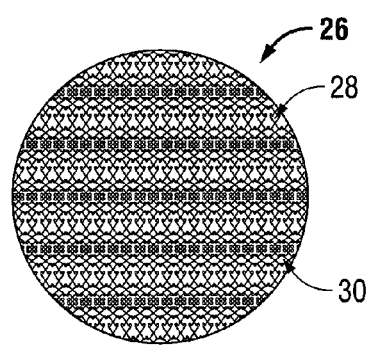

With reference to FIG. 2B, the prosthetic knit mesh 26 is smaller than the grip-type knit mesh 22 (FIG. 2A). The prosthetic knit mesh 26 has principal cells 28 and peripheral cells 30. As shown, the peripheral cells 30 are smaller than the principal cells 28. The spiked naps of the grip-type knit mesh grip into cells 28, 30 of the prosthetic knit mesh 26 to form a combination mesh.

Three-dimensional Structure

Figure 3:
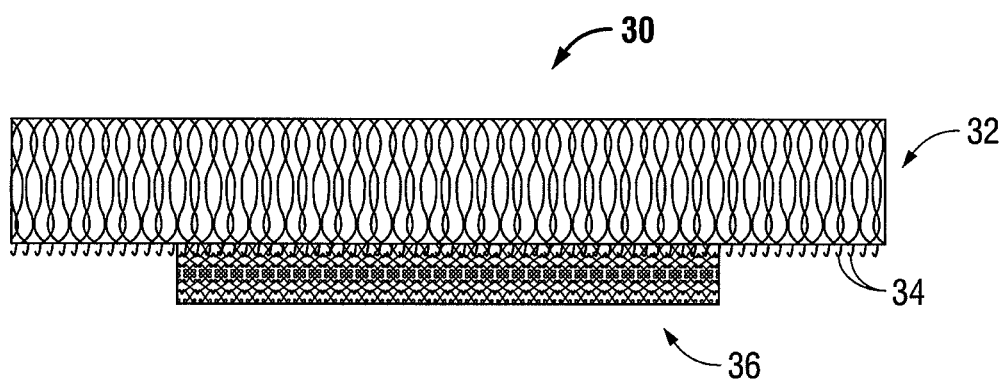
FIG. 3 is a side cross-sectional view showing the combination mesh prior to forming a three-dimensional structure.

Prior to forming a three-dimensional structure, the combination mesh is formed. As shown in FIG. 3, the combination mesh 30 is formed by fastening the prosthetic knit mesh 36 to the grip-type knit mesh 32 via spiked naps 34. If necessary, the prosthetic knit mesh 36 may be unfastened and reattached to the spiked naps 34 of grip-type knit mesh 32. For example, the prosthetic knit mesh 36 may be unfastened and reattached to better secure the prosthetic knit mesh 36 to the grip-type knit mesh 32, or to relocate the prosthetic knit mesh 36 with respect to grip-type knit mesh 32.

With reference to FIGS. 4A and 4B, the three-dimensional structure of the combination mesh 40 can be formed with spiked naps 44, facing outward relative to the three-dimensional structure. The prosthetic knit mesh 46 is also on the outward facing side of the combination mesh 40. The prosthetic knit mesh 46 is attached to the spiked naps 44 of the grip-type knit mesh 42. The porous portion 48 of the grip-type knit mesh 42 is facing inward relative to the three-dimensional structure.

As shown in FIG. 4A, the prosthetic knit mesh 46 covers a portion of grip-type knit mesh 42, but does not cover the entire grip-type knit mesh 42. Spiked naps 44 are exposed at the upper portion of the combination mesh 40. FIG. 4A depicts a folded, self-gripping three-dimensional combination mesh 40.

In embodiments, the mesh can be pinched into a shape rather than folded. With reference to FIG. 4B, combination mesh 50 includes prosthetic knit mesh 56 and grip-type knit mesh 52. Grip-type knit mesh 52 includes spiked naps 54 and porous side 58. With reference to FIG. 4C, the grip-type knit mesh 52 may include alternating sections of spiked naps 54 and pores 60 (such as form porous side 58) along the top edge 62 of the grip-type knit mesh 52. This allows the spiked naps 54 to grip the pores 60 in a fan-like manner along the top edge 62 of the grip-type knit mesh 52, thereby forming the combination mesh 50 into a pinched cone three-dimensional structure.

The spiked naps may grip to the porous portion of the grip-type knit mesh and/or the cells of the prosthetic knit mesh in such a manner as to be secure yet capable of being detached and reattached as necessary. The combination mesh may be formed or folded into a three-dimensional structure. For example, the knit may be formed or folded into a cone, cylinder, triangle, square, and the like. In embodiments, the three-dimensional structure can be held together by using the naps engaged with the open pore or cell structure wherever there is overlap.

In embodiments, the surgeon can form the mesh into the desired shape prior to using the mesh in situ. In embodiments, markings on the grip-type knit mesh and/or prosthetic knit mesh can provide guidance as to how to fold or form the mesh into a three-dimensional structure.

Methods of Use

In accordance with the present disclosure, the three-dimensional combination mesh may be used in either minimally invasive or open surgery. A minimally invasive method of treating a hernia includes: making an incision in the abdominal wall close to the herniated area; making a subcutaneous cut, through the incision, over and surrounding the area of the hernia; inserting a three-dimensional combination mesh through the incision using a laparoscopic device; and inserting the three-dimensional combination mesh into the hernia.

Thus, a combination mesh according to the present disclosure can be inserted through a small incision (e.g., from about 1 cm to about 2 cm in length) in the abdominal cavity. In embodiments, a hernia region is reached using an anterior surgical approach. The combination mesh is formed by fastening a prosthetic mesh to a grip-type knit mesh via the spiked naps. The combination mesh is then formed into a three-dimensional structure by fastening a grip portion to a porous portion of the mesh. The three-dimensional structure may mirror the three-dimensional structure of the defect. The mesh is then inserted through the opening in the tissue wall until the base lies flush with or slightly beyond the defect. The spiked naps along the top edge of the combination mesh are facing outward and will grip to the tissue securing the mesh within the tissue. The combination mesh thus conforms to the shape of the defect and adheres to the surrounding tissue in such a way as to secure the combination mesh to the tissue. It is also contemplated that a surgical fastener is used to attach the combination mesh to the surrounding tissue. In embodiments where the spiked naps of the grip-type knit mesh are formed from a biodegradable material such as, for example, a polylactic acid (PLA), the grip-type knit mesh is formed from a non-biodegradable material such as, for example, monofilament polyester of polyethylene terephthalate (PET), and the prosthetic mesh is formed from monofilament propylene, the spiked naps of the mesh will degrade over time while the non-degradable portions of the combination mesh remain to provide stability to the combination mesh. This results in less foreign material left in the patient than when a fully non-biodegradable mesh is used.

A separate mesh may also be adhered to the surrounding tissue.

Figure 5A:
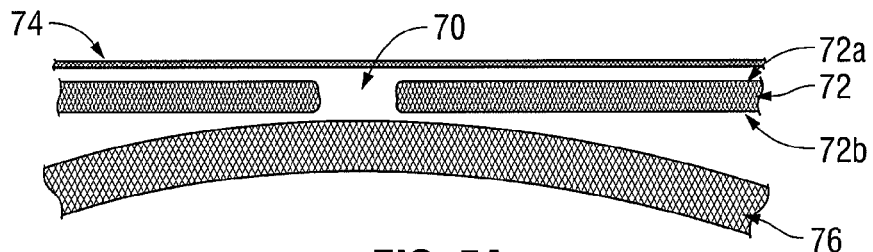
FIGS. 5A-D are side cross-sectional views showing the use of the combination mesh in a hernia repair.
Figure 5B:
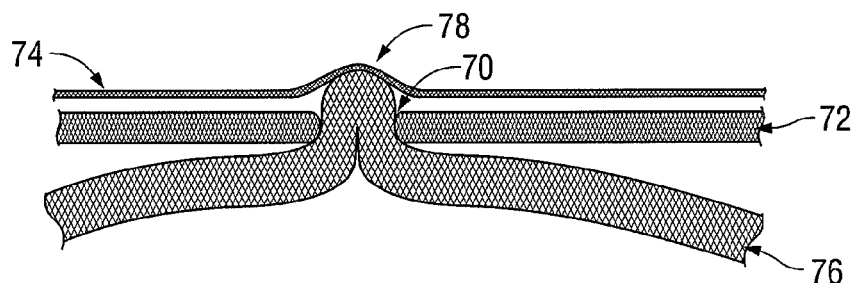

Referring now to FIGS. 5A-5D, a method of using a three-dimensional combination mesh to perform a surgical repair procedure is shown and described. With reference to FIG. 5A, a hernia may involve a tear 70, in the abdominal wall 72. Abdominal wall 72 is defined by an external side 72a and peritoneum 72b. A surface tissue 74, which covers the external side 72a of abdominal wall 72, may or may not be immediately affected by this tear 70. An internal organ 76, located below the peritoneum 72b of the abdominal wall 72, may not protrude until some form of exertion or use of the muscle located at the abdominal wall 72 forces the internal organ 76 into the tear 70. Depending on the size and location of the tear 70, exertion may not be needed to cause the organ 76 to protrude. As shown in FIG. 5B, a hernia occurs when internal organ 76 protrudes into the tear 70 of abdominal wall 72. Oftentimes the protrusion creates a bulge 78 in the surface tissue 74.

Figure 5C:
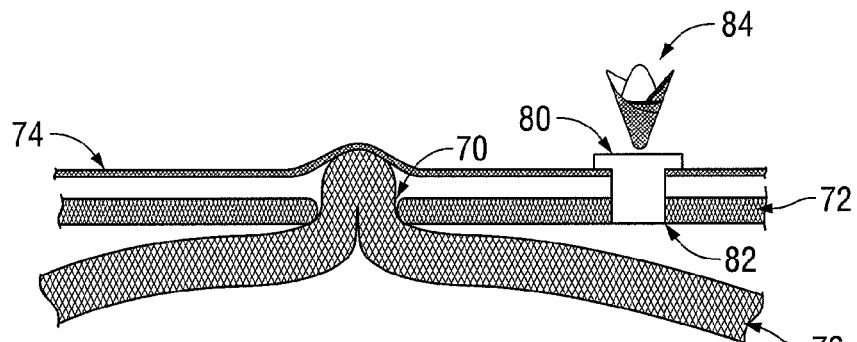
Figure 5D:
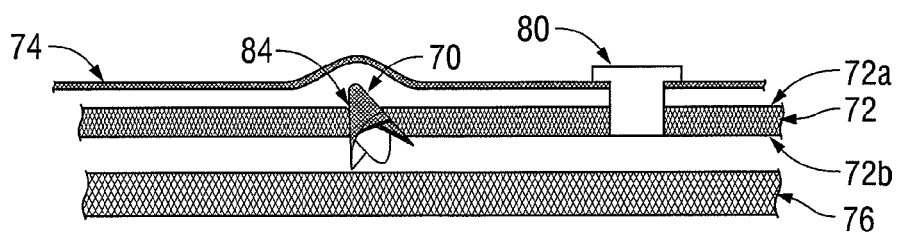

In order to correct the defect, as depicted in FIG. 5C, an incision 82 is made through the abdominal wall 72 in close proximity to tear 70 and a three-dimensional combination mesh 84 is inserted using a trocar 80 or similar laparoscopic device. As shown in FIG. 5D, a three-dimensional grip-type knit mesh 84 is then placed in the tear 70 from the peritoneum 72b of the abdominal wall 72. The spiked naps attach to the abdominal wall 72 and allow the three-dimensional combination mesh 84 to fill the tear 70 in the abdominal wall 72 and return the internal organ 76 to its original location.

While the above description contains many specifics, these specifics should not be construed as limitations on the scope of the present disclosure, but merely as exemplifications of preferred embodiments thereof. For example, in embodiments the prosthetic knit mesh may be applied to the smooth side (the side having no spiked naps) of the grip-type knit mesh. In such embodiments, the prosthetic knit mesh may be secured to the grip-type knit mesh using techniques within the purview of those skilled in the art, including, but not limited to adhesives, sewing, ultrasonic welding and the like. Those skilled in the art will envision many other possible variations that are within the scope and spirit of the present invention.

We claim:

1. A compound three-dimensional surgical implant comprising:
   a grip-type knit mesh defining pores and including a plurality of spiked naps extending from a surface the grip-type knit mesh;
   a prosthetic knit mesh defining principal cells and peripheral cells being layered on the grip-type knit mesh such that at least a first portion of the spiked naps grip at least a portion of the prosthetic knit mesh, wherein the prosthetic knit mesh is smaller in surface area than the grip-type knit mesh;

the grip-type knit mesh and the prosthetic knit mesh being folded together into a predetermined three-dimensional structure such that at least a second portion of the spiked naps grip at least a portion of the pores of the grip-type knit mesh to hold the three-dimensional structure of the surgical implant.

2. The compound three-dimensional surgical implant of claim 1, wherein the grip-type knit mesh and the prosthetic knit mesh comprise materials selected from the group consisting of biodegradable, non-biodegradable, and combinations thereof.

3. The compound three-dimensional surgical implant of claim 1, wherein the material defining the pores of the grip-type knit mesh is non-biodegradable.

4. The compound three-dimensional surgical implant of claim 3, wherein the material defining the spiked naps of the grip-type knit mesh is biodegradable.

5. The compound three-dimensional surgical implant of claim 4, wherein the biodegradable material defining the spiked naps is selected from the group consisting of polylactic acid, polyglycolic acid, poly(lactide-co-(ε-caprolactone)), poly(glycolide-co-α-caprolactone)), poly(lactide-co-glycolide), and combinations thereof.

6. The compound three-dimensional surgical implant of claim 4, wherein the material defining the prosthetic knit mesh is non-biodegradable.

7. The compound three-dimensional surgical implant of claim 6, wherein the non-biodegradable material defining the pores is selected from the group consisting of polyethylenes, polypropylenes, ultra high molecular weight polyethylene, and combinations thereof.

8. The compound three-dimensional surgical implant of claim 3, wherein the non-biodegradable material defining the pores is selected from the group consisting of polyethylenes, polypropylenes, ultra high molecular weight polyethylene, and combinations thereof.

9. The compound three-dimensional surgical implant of claim 1, wherein the predetermined three-dimensional structure is conical.

10. The compound three-dimensional surgical implant of claim 1, further comprising a bioactive agent.

11. The compound three-dimensional surgical implant of claim 10, wherein the bioactive agent is selected from the group consisting of anesthetics, analgesics, and antispasmodics.

12. The compound three-dimensional surgical implant of claim 1, wherein the spiked naps are each from about 1 mm to about 2 mm in length.

13. The compound three-dimensional surgical implant of claim 1, wherein the density of spiked naps on the grip-type knit mesh is from about 50 to about 90 spiked naps per square centimeter.

14. The compound three-dimensional surgical implant of claim 1, wherein the principal cells of the prosthetic knit mesh have a diameter from about 1 mm to about 2 mm.

15. The compound three-dimensional surgical implant of claim 1, wherein the peripheral cells of the prosthetic knit mesh have a diameter from about 0.4 mm to about 0.8 mm.

16. The compound three-dimensional surgical implant of claim 1, wherein the peripheral cells allow the spiked naps of the grip-type knit mesh to grip the prosthetic knit mesh and the principal cells allow for tissue ingrowth in situ.

17. A compound three-dimensional surgical implant comprising:
a grip-type knit mesh defining pores and including a plurality of spiked naps extending from a surface thereof and a prosthetic knit mesh defining principal and/or peripheral cells located on the grip-type knit mesh, wherein the prosthetic knit mesh is smaller in surface area than the grip-type knit mesh and whereby at least a first portion of the spiked naps of the grip-type knit mesh grip the principal cells and/or peripheral cells of the prosthetic knit mesh forming a compound mesh and whereby the compound three-dimensional surgical implant is formed by folding the compound mesh into a predetermined three-dimensional structure such that at least a second portion of the spiked naps grip at least a portion of the pores to hold the three-dimensional structure of the compound three-dimensional surgical implant.

* * * * *